(12) United States Patent
Nozawa (10) Patent No.: US 10,918,842 B2
(45) Date of Patent: Feb. 16, 2021

(54) BALLOON CATHETER

(71) Applicant: TERUMO KABUSHIKI KAISHA, Tokyo (JP)

(72) Inventor: Naoto Nozawa, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 362 days.

(21) Appl. No.: 15/819,110

(22) Filed: Nov. 21, 2017

(65) Prior Publication Data

US 2018/0147396 A1    May 31, 2018

(30) Foreign Application Priority Data

Nov. 30, 2016    (JP) .................................. 2016-233116

(51) Int. Cl.
  *A61F 2/958*    (2013.01)
  *A61M 29/02*    (2006.01)
  *A61M 25/10*    (2013.01)
  *A61F 2/90*    (2013.01)

(52) U.S. Cl.
  CPC ............. *A61M 29/02* (2013.01); *A61F 2/958* (2013.01); *A61F 2/90* (2013.01); *A61F 2230/0008* (2013.01); *A61F 2230/0067* (2013.01); *A61F 2250/0039* (2013.01); *A61M 25/104* (2013.01); *A61M 25/1011* (2013.01); *A61M 2025/1013* (2013.01)

(58) Field of Classification Search
  CPC .. A61F 2/958; A61F 2/95; A61F 2/966; A61F 2/07; A61F 2/06; A61F 2/954; A61M 29/02; A61M 25/1011
  See application file for complete search history.

(56) References Cited

U.S. PATENT DOCUMENTS 5,304,135 A * 4/1994 Shonk ................ A61M 25/1011
  604/101.01
2011/0143014 A1* 6/2011 Stankus .................. A61F 2/958
  427/2.14

FOREIGN PATENT DOCUMENTS

JP    2001-515772 A    9/2001

* cited by examiner

*Primary Examiner* — Vi X Nguyen
(74) *Attorney, Agent, or Firm* — Buchanan Ingersoll & Rooney PC (57) ABSTRACT

A balloon catheter has a first shaft that includes a first lumen, and that extends in an axial direction, a first balloon disposed on a distal side of the first shaft, and capable of being expanded and contracted in a radial direction, a second shaft that includes a second lumen, and that extends in the axial direction, and a second balloon disposed on a distal side of the second shaft so as to cover an outer periphery of the first balloon, and that is capable of being expanded and contracted in the radial direction. The first shaft is configured to be movable in the axial direction relative to the second shaft, and the first balloon is configured to be movable in the axial direction relative to the second balloon in response to movement of the first shaft.

19 Claims, 8 Drawing Sheets

BALLOON CATHETER

CROSS-REFERENCES TO RELATED APPLICATIONS

This application claims priority to Japanese Application No. 2016-233116 filed on Nov. 30, 2016, the entire content of which is incorporated herein by reference.

TECHNICAL FIELD

The present invention generally relates to a balloon catheter and method.

BACKGROUND DISCUSSION

In the medical field, a balloon catheter is widely known which is used in carrying out a medical procedure for widening a lesion area (stenosed site or the like) formed inside a body lumen, or in causing a stent to be indwelled in the lesion area. In carrying out the medical procedure using the balloon catheter, in some cases, a plurality of balloon catheters are used in order to widen the lesion area or to expand the stent multiple times. If the plurality of balloon catheters are prepared and used, the cost required for the medical procedure increases correspondingly, thereby resulting in poor medical cost performance in the medical procedure carried out using the balloon catheter.

For example, Japanese Application Publication No. JP-T-2001-515772 discloses a balloon catheter including two balloons in which one balloon is disposed so as to cover an outer periphery of the other balloon. The medical procedure for widening the lesion area is carried out, or the stent is caused to indwell the lesion area by dilating one balloon. Thereafter, the lesion area can be further widened or the stent can be further expanded by the other balloon. Therefore, without exchanging the catheter, treatment can be performed multiple times using one balloon catheter.

SUMMARY

However, according to Japanese Application Publication No. JP-T-2001-515772 described above, a relative position of the other balloon to the one balloon is fixed, thereby limiting a range expandable by the other balloon after the lesion area is widened or the stent is expanded by one balloon. Therefore, in some cases, without widening an insufficiently widened site, restenosis occurs in the lesion area, or the stent is insufficiently expanded. Thus, a site other than the widening target site may be excessively widened.

The balloon catheter disclosed here is made in view of the above-described problems. The disclosed balloon catheter can locally widen or enlarge a stenosed site or locally expand an insufficiently widened site of a stent while reducing the likelihood of or preventing poor medical cost performance caused by using a plurality of balloon catheters.

A balloon catheter comprises: a first shaft that includes a first lumen enabling a pressurizing medium to circulate therethrough, and that extends in an axial direction; a first balloon disposed on a distal side of the first shaft, with the first balloon being deformable in a radially expandable manner in response to supply of the pressurizing medium to the first balloon via the first lumen and being deformable in a radially contractible manner in response to discharge of the pressurizing medium from the first balloon via the first lumen; a second shaft that includes a second lumen enabling the pressurizing medium to circulate therethrough, and that extends in the axial direction; and a second balloon disposed on a distal side of the second shaft and covering an outer periphery of the first balloon, with the second balloon being deformable in a radially expandable manner in response to supply of the pressurizing medium to the second balloon via the second lumen and being deformable in a radially contractible manner in response to discharge of the pressurizing medium via the second lumen. The first shaft is movable in the axial direction relative to the second shaft, and the first balloon is movable in the axial direction relative to the second balloon in response to movement of the first shaft.

According to the balloon catheter having the above-described configuration, the first balloon can be moved relative to the second balloon in the axial direction. Accordingly, an insufficiently widened site of a lesion area can be locally widened or an insufficiently expanded site of a stent can be locally expanded by the first balloon. In this manner, it is possible to inhibit or prevent restenosis of the lesion area or insufficient expansion of the stent. In addition, one balloon catheter can correspond to treatment performed multiple times, such as indwelling and supplementary expansion of the stent. Accordingly, it is possible to reduce the number of balloon catheters to be prepared and used during a medical procedure. In this manner, it is possible to inhibit or prevent poor medical cost performance caused by preparing and using a plurality of balloon catheters.

According to another aspect, a balloon catheter positionable in a blood vessel comprises: a first balloon possessing an interior and being radially expandable in response to supply of a pressurizing medium to the interior of the first balloon and being radially contractible in response to discharge of the pressurizing medium from the interior of the first balloon; a second balloon positioned in covering relation to the first balloon so that the first balloon is positioned inside the second balloon, with the second balloon possessing an interior and being radially expandable in response to supply of the pressurizing medium to the interior of the second balloon and radially contractible in response to discharge of the pressurizing medium from the interior of the second balloon; a first lumen in communication with the interior of the first balloon to supply the pressurizing medium to the interior of the first balloon and to discharge the pressurizing medium from the interior of the first balloon; and a second lumen in communication with the interior of the second balloon to supply the pressurizing medium to the interior of the second balloon and to discharge the pressurizing medium from the interior of the second balloon, the second lumen being separate from the first lumen. The first balloon is axially movable relative to the second balloon to position the first balloon at different positions relative to the second balloon, and the first balloon is less compliant than the second balloon.

In accordance with another aspect, a method comprises: introducing a balloon catheter into a blood vessel, wherein the balloon catheter comprises: first and second balloons each possessing an interior, with the first balloon positioned inside the second balloon; a first lumen in communication with the interior of the first balloon; and a second lumen in communication with the interior of the second balloon, with the second lumen being different from the first lumen. The method further involves moving the balloon catheter in the blood vessel to position the second balloon at a stenosed site in the blood vessel, outwardly expanding the second balloon toward the stenosed site by introducing pressurizing fluid into the interior of the second balloon by way of the second lumen; inwardly contracting the second balloon away from the stenosed site by discharging the pressurized fluid out of the interior of the second balloon by way of the second lumen; axially moving the first balloon relative to the second balloon after the inwardly contracting of the second balloon; and outwardly expanding the first balloon by introducing pressurizing fluid into the interior of the first balloon by way of the first lumen. The outward expansion of the first balloon occurs after the axially moving of the first balloon, and the outward expansion of the first balloon is performed to cause the first balloon to contact the second balloon and outwardly expand the second balloon toward the stenosed site.

BRIEF DESCRIPTION OF THE DRAWINGS

FIGS. 4(a)-4(D) are schematic views of a medical procedure example of the stent delivery system according to the embodiment.

FIGS. 5(A)-5(C) are schematic sectional views of the stent delivery system for embodying the medical procedure example illustrated in FIG. 4.

FIGS. 6(A)-6(D) are schematic views illustrating a medical procedure example of a stent delivery system according to a comparative example.

FIGS. 8(A)-8(C) are schematic views illustrating a medical procedure example of the balloon catheter according to the modification example.

DETAILED DESCRIPTION

Set forth below with reference to the accompanying drawings is a detailed description of embodiments of a balloon catheter representing examples of the inventive balloon catheter disclosed here. The following description does not limit the technical scope or the meaning of terms described in the appended claims. In addition, dimensional proportions in the drawings are exaggerated and different from actual proportions for convenience of description, in some cases.

A balloon catheter 100 according to one embodiment is configured to serve as a balloon catheter used for a stent delivery system 10 in which a balloon expandable stent (hereinafter, referred to as a stent) 200 is mounted (installed) on balloons 130 and 140 in a deflated state. As will be described later, in the present embodiment, a medical procedure example will be described in which the stent 200 is caused to be indwelled at a stenosed site N formed in a blood vessel V (refer to FIGS. 4 and 5). However, an indwelling position of the stent 200 is not particularly limited. For example, the position may be a lesion area such as a stenosed site appearing in biliary ducts, bronchial tubes, esophagi, urethrae, or other body lumens.

Figure 1:
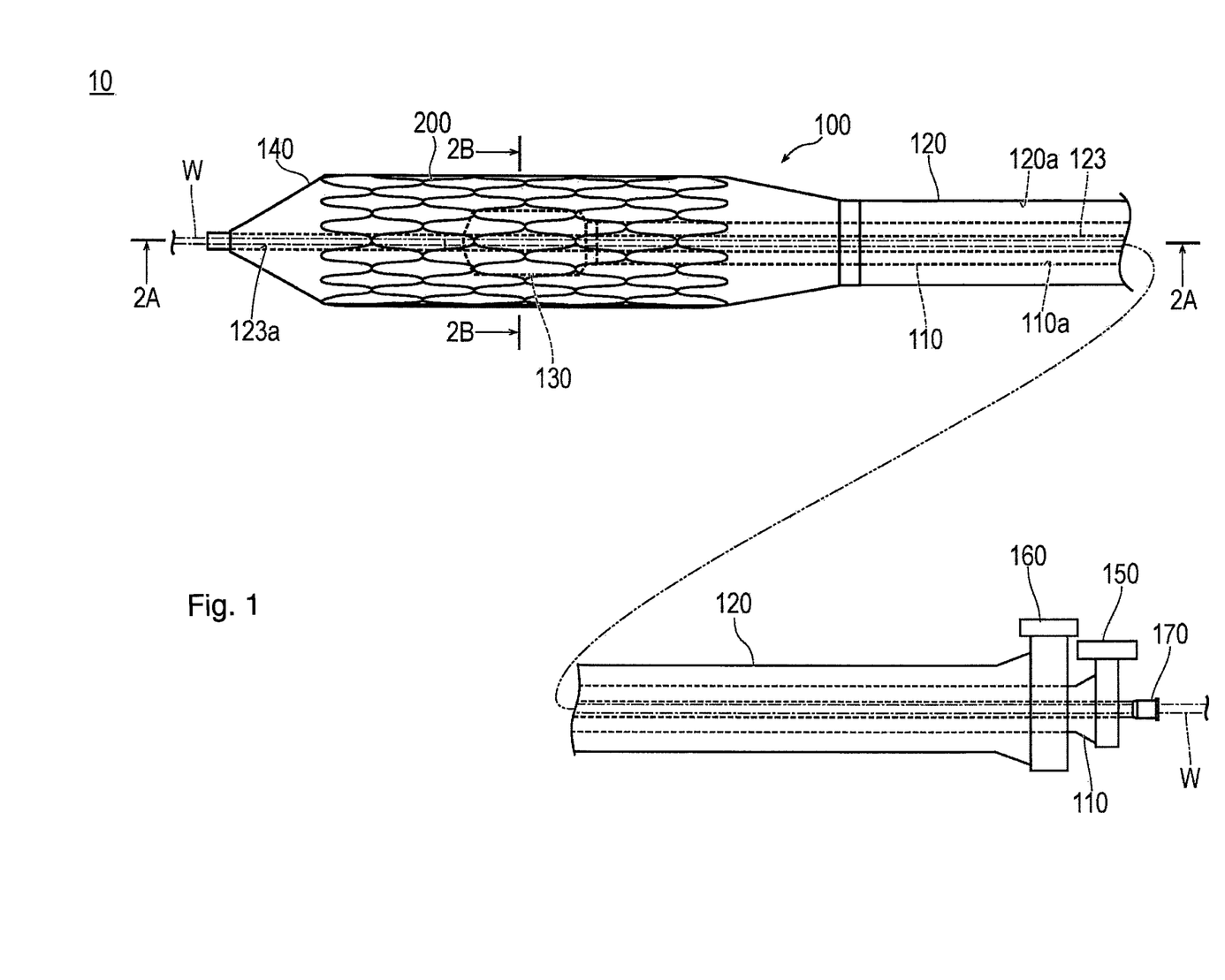
FIG. 1 is a view illustrating an overall configuration of a stent delivery system according to an embodiment.

In the description herein, a side (side on which the balloons 130 and 140 illustrated on the left side in FIG. 1 are arranged) inserted into a body lumen in the balloon catheter 100 is referred to as a distal side. A side (side on which ports 150, 160, and 170 illustrated on the right side in FIG. 1 are arranged) located on a side opposite to the distal side so as to allow a hand-side operation is referred to as a proximal side. A distal portion means a prescribed range including a distal end (most distal end) and the periphery, and a proximal portion means a prescribed range including a proximal end (most proximal end) and the periphery. In addition, a direction in which an inner balloon shaft 110 and an outer balloon shaft 120 of the balloon catheter 100 stretch is referred to as an axial direction, and a direction orthogonal to the axial direction is referred to as a radial direction.

The stent delivery system 10 will be described with reference to FIGS. 1 to 3.

As illustrated in FIG. 1, the balloon catheter 100 has the inner balloon shaft 110 (corresponding to a first shaft) extending in the axial direction, the inner balloon (corresponding to a first balloon) 130 disposed on the distal side or distal end portion of the inner balloon shaft 110, the outer balloon shaft 120 (corresponding to a second shaft) extending in the axial direction similarly to the inner balloon shaft 110, and the outer balloon (corresponding to a second balloon) 140 disposed on the distal side or distal end portion of the outer balloon shaft 120 so as to cover an outer periphery of the inner balloon 130. As illustrated in FIGS. 1 and 3, an inner balloon port 150 is disposed in the proximal portion of the inner balloon shaft 110, and an outer balloon port 160 and a guide wire port 170 are respectively disposed in the proximal portion of the outer balloon shaft 120. In the description below, referees to the "balloons 130 and 140" may refer to both the inner balloon 130 and the outer balloon 140, or may refer to only one of them, in some cases.

Figure 2A:
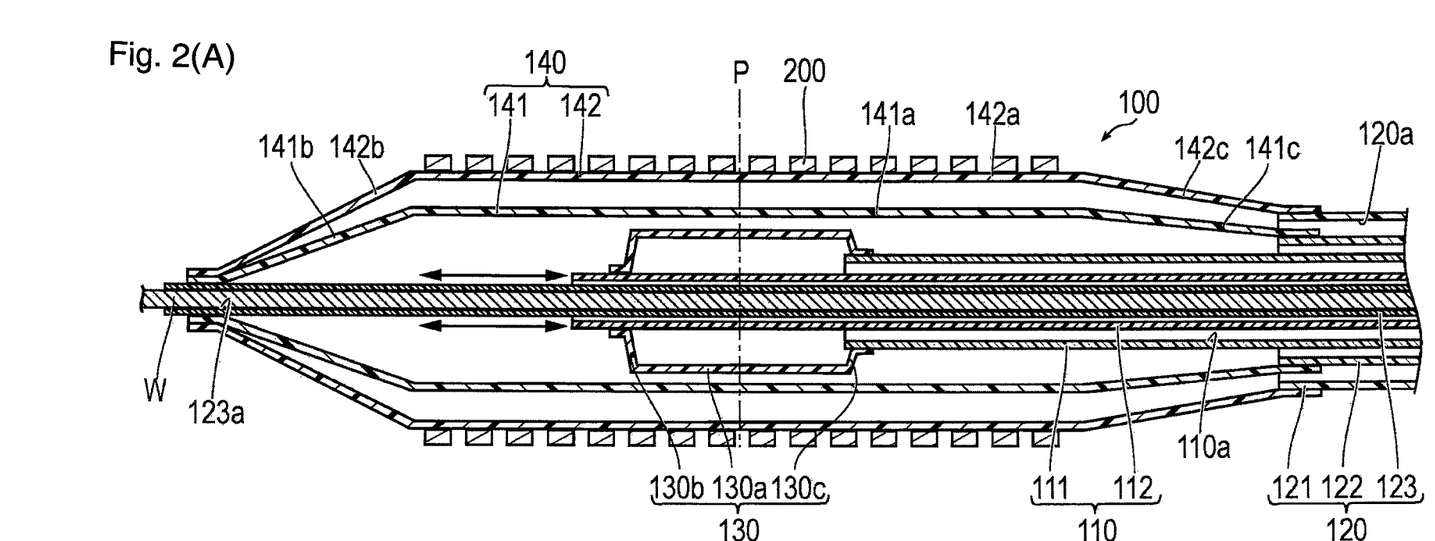
FIG. 2(A) is an axially parallel sectional view on a distal side of the stent delivery system which is taken along the section line 2A-2A illustrated in FIG. 1.
Figure 2B:
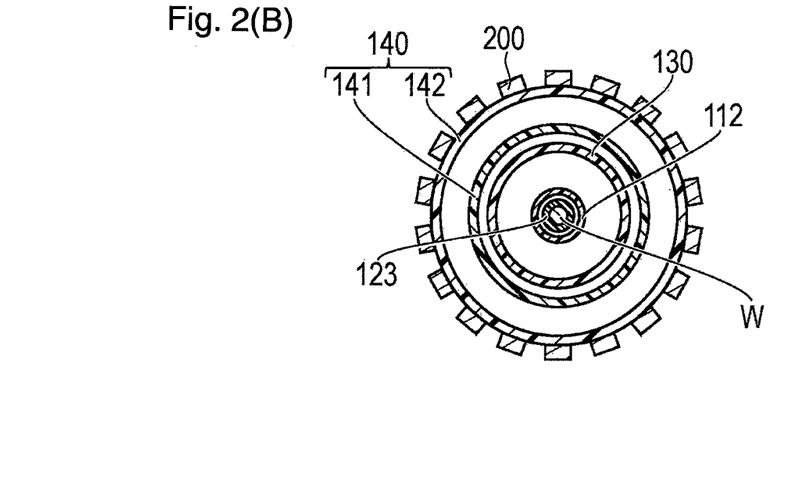
FIG. 2(B) is an axially orthogonal sectional view on the distal side of the stent delivery system which is taken along the section line 2B-2B illustrated in FIG. 1.

As illustrated in FIGS. 2(A) and 2(B), the inner balloon shaft 110 includes an inner balloon outer tube 111 serving as a tubular body whose distal end and proximal end are open, and an inner balloon inner tube 112 disposed in a lumen of the inner balloon outer tube 111.

An inner balloon dilating lumen (corresponding to a first lumen) 110a which circulates a pressurizing medium for dilating the inner balloon 130 is formed between the inner balloon outer tube 111 (inner surface of the inner balloon outer tube 111) and the inner balloon inner tube 112 (outer surface of the inner balloon inner tube 111). The inner balloon dilating lumen 110a communicates with the interior of the inner balloon 130. In addition, an outer balloon inner tube 123 (to be described later) is disposed in the lumen of the inner balloon inner tube 112. The inner balloon inner tube 112 is configured to be movable forward and rearward in the axial direction relative to the outer balloon inner tube 123. That is, the inner balloon shaft 110 is configured to be movable forward and rearward in the axial direction relative to the outer balloon shaft 120.

As illustrated in FIGS. 2(A) and 2(B), the outer balloon shaft 120 includes a first outer balloon outer tube 121 serving as a tubular body whose distal end and proximal end are open, a second outer balloon outer tube 122 disposed in the lumen of the first outer balloon outer tube 121, and the outer balloon inner tube 123 disposed in the lumen of the second outer balloon outer tube 122.

An outer balloon dilating lumen (corresponding to a second lumen) 120a which circulates the pressurizing medium for dilating the outer balloon 140 is formed between the first outer balloon outer tube 121 (inner surface of the first outer balloon outer tube) and the second outer balloon outer tube 122 (outer surface of the second outer balloon outer tube). The outer balloon dilating lumen 120a communicates with the interior of the outer balloon 140. In the illustrated embodiment, the inner balloon dilating lumen 110a and the outer balloon dilating lumen 120a are different and separate from one another. The inner balloon shaft 110 is inserted or positioned between the second outer balloon outer tube 122 and the outer balloon inner tube 123. The lumen of the outer balloon inner tube 123 has a guide wire lumen 123a into which a guide wire W is inserted in order to guide the balloon catheter 100 to a lesion area.

According to the above-described configuration, the inner balloon dilating lumen 110a and the outer balloon dilating lumen 120a for dilating the inner balloon 130 and the outer balloon 140 are independently disposed. Accordingly, deflated and dilated states of the inner balloon 130 and deflated and dilated states of the outer balloon 140 can be individually adjusted. In this manner, a selection range of the medical procedure using the balloon catheter 100 is increased or expanded. Accordingly, the balloon catheter 100 is applicable to a wide range of medical procedures.

The inner balloon shaft 110 and the outer balloon shaft 120 are preferably formed of a material which is flexible to some degree. For example, this material includes polyolefin such as polyethylene, polypropylene, polybutene, ethylene-propylene copolymer, ethylene-vinyl acetate copolymer, ionomer, or a mixture of two or more of these materials, thermoplastic resin such as polyvinyl chloride resin, polyamide, polyamide elastomer, polyester, polyester elastomer, polyurethane, and fluororesin, silicone rubber, or latex rubber.

The inner balloon 130 is configured to be capable of being deformed in a dilated or expanded manner and being deformed in a deflated or contracted manner in the radial direction in response to supply and discharge of the pressurizing medium. As illustrated in FIGS. 2(A) and 2(B), the inner balloon 130 has a cylindrical portion 130a including a substantially constant outer diameter in the axial direction (lateral direction in FIGS. 1 and 2), a distal side tapered portion 130b which is formed on the distal side or distal end of the cylindrical portion 130a and whose outer diameter gradually decreases toward the distal side, and a proximal side tapered portion 130c which is formed on the proximal side or proximal end of the cylindrical portion 130a and whose outer diameter gradually decreases toward the proximal side. It is preferable that each axial length of the distal side tapered portion 130b and the proximal side tapered portion 130c of the inner balloon 130 is as short as possible. In this manner, when the inner balloon 130 moves inside the outer balloon 140 in the axial direction, it is possible to inhibit or prevent the inner balloon 130 from interfering with the inner side of an inner layer 141 of the outer balloon 140. The inner balloon 130 may have a configuration without the distal side tapered portion 130b and the proximal side tapered portion 130c. In this case, when dilated, the inner balloon 130 has a substantially rectangular parallelepiped shape in a cross section parallel to the axial direction.

The proximal portion of the inner balloon 130 is fixed to the distal portion of the inner balloon outer tube 111, and the distal portion of the inner balloon 130 is fixed to the distal portion of the inner balloon inner tube 112. A space communicating with the inner balloon dilating lumen 110a is formed or exists between the inner balloon 130 and the inner balloon inner tube 112. The space is hermetically formed, and constitutes a pressurizing region which can apply pressure to the inner balloon 130 so as to deform the balloon 130 in a dilated manner in response to the inflow of the pressurizing medium.

The outer balloon 140 is configured to spread or expand the stent 200 from the inner side in the radial direction so as to be dilated or expanded as the outer balloon 140 is dilated outward in the radial direction. The outer balloon 140 has the inner layer 141 disposed so as to cover the outer periphery of the inner balloon 130, and an outer layer 142 disposed so as to cover the outer periphery of the inner layer 141. The outer layer 142 is deformable in a dilated or expanded manner and is deformable a deflated or contracted manner in the radial direction in response to supply and discharge of the pressurizing medium. A space communicating with the outer balloon dilating lumen 120a is formed or exists between the inner layer 141 and the outer layer 142. The space is hermetically formed, and constitutes a pressurizing region which can apply pressure to the outer balloon 140 so as to deform the outer balloon 140 in the dilated or expanded manner in response to the inflow of the pressurizing medium.

According to the above-described configuration, the pressurizing region of the inner balloon 130 and the pressurizing region of the outer balloon 140 are formed separately from each other. In this manner, the pressurizing medium of the inner balloon 130 and the pressurizing medium of the outer balloon 140 do not mix with each other. Accordingly, for example, it is possible to inhibit or prevent a disadvantage that the pressurizing medium of the outer balloon 140 may flow back to the proximal side through the portion between the inner balloon inner tube 112 and the outer balloon inner tube 123. In addition, the space (gap) is formed so as to divide (partition) the pressurizing region between the inner balloon 130 and the outer balloon 140. Accordingly, the inner balloon 130 can be more smoothly moved in the axial direction.

The inner layer 141 of the outer balloon 140 has a cylindrical portion 141a having a substantially constant outer diameter in the axial direction (lateral direction in FIGS. 1 and 2), a distal side tapered portion 141b that is formed or exists on the distal side of the cylindrical portion 141a and whose outer diameter gradually decreases toward the distal side, and a proximal side tapered portion 141c that is formed or exists on the proximal side of the cylindrical portion 141a and whose outer diameter gradually decreases toward the proximal side.

Similarly, the outer layer 142 of the outer balloon 140 has a cylindrical portion 142a having a substantially constant outer diameter in the axial direction (lateral direction in FIGS. 1 and 2), a distal side tapered portion 142b that is formed or exists on the distal side of the cylindrical portion 142a and whose outer diameter gradually decreases toward the distal side, and a proximal side tapered portion 142c that is formed or exists on the proximal side of the cylindrical portion 142a and whose outer diameter gradually decreases toward the proximal side.

The proximal portion of the inner layer 141 of the outer balloon 140 is fixed to the distal portion of the second outer balloon outer tube 122, and the distal portion of the inner layer 141 is fixed to the distal portion of the outer balloon inner tube 123. In addition, the proximal portion of the outer layer 142 of the outer balloon 140 is fixed to the distal portion of the first outer balloon outer tube 121, and the distal portion of the outer layer 142 is fixed to the distal portion of the outer balloon inner tube 123 via the inner layer 141.

In a deflated state, the balloons 130 and 140 are folded so as to wrap around the outer periphery of the inner balloon inner tube 112 and the outer balloon inner tube 123. The stent delivery system 10 in a state where the balloons 130 and 140 are folded is omitted in the illustration.

The cylindrical portion 142a of the outer layer 142 of the outer balloon 140 configures an effectively dilatable portion in which the outer balloon 140 applies a dilating force to the stent 200. In addition, a portion where the cylindrical portion 130a of the inner balloon 130 and the cylindrical portion 142a of the outer layer 142 of the outer balloon 140 overlap each other in the axial direction constitutes an effectively dilatable portion in which the inner balloon 130 applies the dilating force to the stent 200. In addition, a range in which the cylindrical portion 141a of the inner layer 141 of the outer balloon 140 stretches in the axial direction corresponds to a movable range in which the inner balloon 130 is movable forward and rearward in the axial direction. Without being limited to the above-described configuration, the movable range of the inner balloon 130 can be appropriately changed depending on the medical procedure.

It is preferable that a dilated diameter of the cylindrical portion 130a of the inner balloon 130 (hereinafter, referred to as a dilated diameter of the inner balloon 130) when the internal pressure of the inner balloon 130 reaches nominal pressure is formed to be larger than a dilated diameter of the cylindrical portion 142a of the outer layer 142 of the outer balloon 140 (hereinafter, referred to as a dilated diameter of the outer balloon 140) when internal pressure of the outer balloon 140 reaches nominal pressure. Nominal pressure generally refers to the recommended pressure. This includes the pressure needed to expand the balloon to the appropriate diameter. This recommended pressure may be indicated on a package insert which indicates an associated expanded diameter. The user may then pressurize the balloon while viewing a gauge, and when the balloon internal pressure reaches the nominal pressure, the diameter of the balloon will be the diameter associated with the nominal pressure. In this manner, an insufficiently widened or radially outwardly expanded site can be locally expanded by the inner balloon 130. Dimensions such as a size and a shape of the balloons 130 and 140 are appropriately adjusted so that a size relationship between the respective dilated diameters of the balloons 130 and 140 can be obtained as described above. In a state where the balloons 130 and 140 are dilated at the nominal pressure, the dilated diameter of the cylindrical portion 130a of the inner balloon 130 can be approximately 3.25 mm, for example. The dilated diameter of the cylindrical portion 142a of the outer layer 142 of the outer balloon 140 can be approximately 3.00 mm, for example. The dilated diameter means the dilated diameter in a state where the balloons 130 and 140 are respectively dilated by the pressurizing medium, and does not include the dilated diameter of the outer balloon 140 in a state where the outer balloon 140 is dilated by the dilating force of the inner balloon 130 (refer to FIG. 5(A)).

The length along the axial direction of the inner balloon 130 may be smaller than the length along the axial direction of the outer balloon 140. In this manner, the dilating force can be locally applied by the inner balloon 130. The length along the axial direction of the inner balloon 130 can be 3.00 mm to 10.00 mm, for example. The length along the axial direction of the outer balloon 140 can be 20.00 mm to 60.00 mm, for example.

Dimensions such as the dilated diameter of the balloons 130 and 140 or the length along the axial direction can be appropriately changed in accordance with desired treatment content or a treatment target site.

In the present embodiment, it is preferable that the nominal pressure of the inner balloon 130 and the nominal pressure of the outer balloon 140 are set to have approximately the same value. The nominal pressure of the balloons 130 and 140 can be appropriately changed in accordance with product specifications (for example, an outer diameter or a purpose of use) of the balloons 130 and 140 and the stent 200. However, for example, the nominal pressure can be set from 8 atm to 12 atm. The nominal pressure of the inner balloon 130 and the nominal pressure of the outer balloon 140 may also be set to have respectively different values.

It is preferable that the inner balloon 130 is flexible to some degree and has compliance lower than that of the outer balloon 140. In this manner, the inner balloon 130 is formed to have pressure resistance higher than that of the outer balloon 140. That is, the outer balloon 140 is more easily expanded the inner balloon 130. Accordingly, compared to the outer balloon 140, the stronger dilating force can be locally applied to the stent 200.

Herein, the term "compliance" is an index indicating how a shape of the balloon is easily deformed, and means a deformation amount of the balloon per unit increment of the internal pressure of the balloon. The balloon having high compliance is likely to be deformed (more easily deformed)) in response to an increase in the internal pressure of the balloon. Conversely, the balloon having low compliance is less likely (less easily deformed) to be deformed in response to the increase in the internal pressure of the balloon. In addition, the balloon having low compliance has relatively higher pressure resistance, and can apply the relatively stronger dilating force.

As a material for forming the inner balloon 130, it is preferable to use a relatively more rigid material in order to have the compliance lower than that of the outer balloon 140. For example, this material includes polyolefin such as polyethylene, polypropylene, polybutene, ethylene-propylene copolymer, ethylene-vinyl acetate copolymer, ionomer, or a mixture of two or more of these materials, thermoplastic resin such as soft polyvinyl chloride resin, polyamide, polyamide elastomer, polyester, polyester elastomer, polyurethane, and fluororesin, silicone rubber, or latex rubber.

It is preferable that the inner layer 141 of the outer balloon 140 is formed to have the compliance higher than that of the inner balloon 130 and to have compliance lower than that of the outer layer 142. It is this preferable that the inner layer 141 of the outer balloon 140 is more easily compliant or more easily expanded than the inner balloon 130, and that the inner layer 141 of the outer balloon 140 is less easily compliant or less easily expanded than the outer layer 142. In this manner, when the outer layer 142 of the outer balloon 140 is deformed in the dilated our expanded manner, it is possible to inhibit or prevent the inner layer 141 of the outer balloon 140 from being pushed by the pressurizing medium and deformed inward in the radial direction. Therefore, the lumen for allowing the inner balloon 130 to move in the axial direction can be maintained inside in the radial direction of the inner layer 141 of the outer balloon 140. Accordingly, the inner balloon 130 can be more smoothly moved in the axial direction.

As a material for forming the inner layer 141 of the outer balloon 140, in order to have the compliance higher than that of the inner balloon 130 and the compliance lower than that of the outer layer 142, it is preferable to use a material which is less rigid than that of the inner balloon 130 and more rigid than that of the outer layer 142. For example, this material includes polyolefin such as polyethylene, polypropylene, polybutene, ethylene-propylene copolymer, ethylene-vinyl acetate copolymer, ionomer, or a mixture of two or more of these materials, thermoplastic resin such as soft polyvinyl chloride resin, polyamide, polyamide elastomer, polyester, polyester elastomer, polyurethane, and fluororesin, silicone rubber, or latex rubber.

It is preferable that the outer layer 142 of the outer balloon 140 has a higher compliance (is more easily compliant) than that of the inner balloon 130 and the inner layer 141 of the outer balloon 140.

As a material for forming the outer layer 142 of the outer balloon 140, in order to have the compliance higher than that of the inner balloon 130 and the inner layer 141 of the outer balloon 140, it is preferable to use a material which is softer than that of the inner balloon 130 and the inner layer 141 of the outer balloon 140. For example, this material includes polyolefin such as polyethylene, polypropylene, polybutene, ethylene-propylene copolymer, ethylene-vinyl acetate copolymer, ionomer, or a mixture of two or more of these materials, thermoplastic resin such as soft polyvinyl chloride resin, polyamide, polyamide elastomer, polyester, polyester elastomer, polyurethane, and fluororesin, silicone rubber, or latex rubber.

As described above, it is preferable that each portion of the balloons 130 and 140 is configured to have the low compliance in the order of the outer layer 142 of the outer balloon 140, the inner layer 141 of the outer balloon 140, and the inner balloon 130, for example, as in a semi-compliance type, a low-compliance type, and a non-compliance type. In other words, as between the outer layer 142 of the outer balloon 140, the inner layer 141 of the outer balloon 140, and the inner balloon 130, the outer layer 142 of the outer balloon 140 is most compliant, the inner layer 141 of the outer balloon 140 is next most compliant (i.e., has a compliance between the compliance of the outer layer 142 of the outer balloon 140 and the inner balloon 130), and the inner balloon 130 is least compliant.

A method of adjusting the compliance of the outer layer 142 and the inner layer 141 of the outer balloon 140 and the inner balloon 130 is not limited to the method of configuring each portion to include the material having mutually different rigidity or rigidness as described above. For example, a method may be used in which the film thickness of each portion is changed after each portion is fabricated of the same material. In a case of changing the film thickness, the film thickness is formed so as to be thicker in the order of the outer layer 142 of the outer balloon 140, the inner layer 141 of the outer balloon 140, and the inner balloon 130. In other words, as between the outer layer 142 of the outer balloon 140, the inner layer 141 of the outer balloon 140, and the inner balloon 130, the outer layer 142 of the outer balloon 140 is thinnest, the inner layer 141 of the outer balloon 140 is next most thin (i.e., has a thickness between the thickness of the outer layer 142 of the outer balloon 140 and the inner balloon 130), and the inner balloon 130 is least thin (i.e., the inner balloon 130 is thicker than the other two layers 142, 141). In this manner, the compliance can be formed to be lower in the above-described order. In addition, it is also possible to select a known method such as a method of causing the material to partially contain particles for changing the compliance. It is also possible to adjust the exemplified methods in appropriate combinations with each other.

Figure 3:
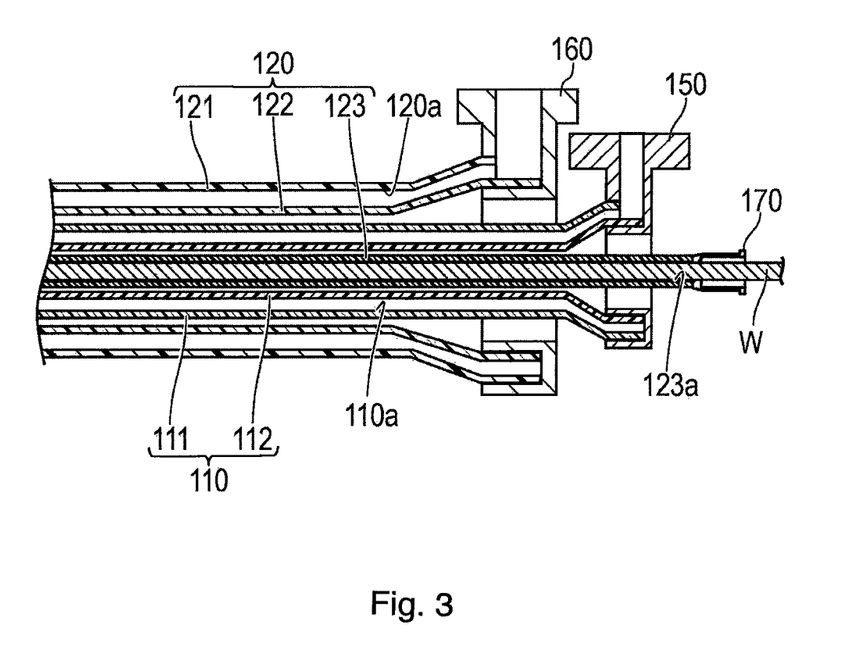
FIG. 3 is an axially parallel sectional view on a proximal side of the stent delivery system.

As illustrated in FIG. 3, the inner balloon port 150 communicates with the inner balloon dilating lumen 110a formed between the inner balloon outer tube 111 and the inner balloon inner tube 112, and causes the pressurizing medium to flow into or to flow out from the inner balloon 130. The inner balloon port 150 is fixedly attached to the proximal portion of the inner balloon shaft 110.

The outer balloon port 160 communicates with the outer balloon dilating lumen 120a formed between the first outer balloon outer tube 121 and the second outer balloon outer tube 122, and causes the pressurizing medium to flows into or to flow out from the outer balloon 140. The outer balloon port 160 is fixedly attached to the proximal portion of the first outer balloon outer tube 121 and the second outer balloon outer tube 122.

The guide wire port 170 communicates with the guide wire lumen 123a formed in the lumen of the outer balloon inner tube 123, and guides the guide wire as the guide wire is introduced or pulled-out. The guide wire port 170 is fixedly attached to the proximal portion of the outer balloon inner tube 123.

The inner balloon port 150 and the outer balloon port 160 can be configured using a known Y-connector, for example. For example, a material for forming the inner balloon port 150, the outer balloon port 160, and the guide wire port 170 includes thermoplastic resins such as polycarbonate, polyamide, polysulfone, polyarylate, and methacrylate-butylene-styrene copolymer.

As illustrated in FIG. 1, the balloon catheter 100 according to the present embodiment is configured to serve as a so-called over-the-wire type catheter in which the guide wire lumen 123a into which the guide wire W is inserted extends over the entirety of the balloon catheter 100 from the distal end to the proximal end of the balloon catheter 100. In this manner, compared to a so-called rapid exchange type catheter, pushing force transmittable performance (pushability) in the axial direction of the inner balloon shaft 110 and the outer balloon shaft 120 can be improved. In this manner, it is possible to smoothly carry out the medical procedure to move the inner balloon 130 forward and rearward relative to the outer balloon 140 in the axial direction.

The pressurizing medium used for dilating the balloons 130 and 140 is preferably a liquid which is likely to be handled when the pressurizing medium is supplied to the balloons 130 and 140. However, gas may be used. For example, as the liquid, a known contrast medium in the medical field is preferably used. However, a physiological salt solution may be used. For example, as the gas, helium gas, $CO_2$ gas, or $O_2$ gas can be used.

The stent 200 according to the present embodiment is a so-called balloon expandable stent which is disposed in a deflated state on the outer periphery of the outer balloon 140 capable of deflating and dilating, and which is deformed in an expanded manner (plastically deformed) by the dilating force of the inner balloon 130 or the outer balloon 140.

The stent 200 is disposed so as to cover the cylindrical portion 142a of the outer layer 142 of the outer balloon 140 folded to wrap around the outer periphery of the inner balloon inner tube 112 and the outer balloon inner tube 123 in a deflated state. The stent 200 is held at the outer periphery of the outer layer 142 of the outer balloon 140 by receiving a compressive force in a state where the stent 200 is disposed so as to cover the outer layer 142 of the outer balloon 140. Hereinafter, a state held in the outer periphery of the outer layer 142 of the outer balloon 140 in a contracted state of the stent 200 is referred to as an "initial state" of the stent delivery system 10.

In the initial state, as illustrated in FIG. 2, it is preferable that a center position (center) of the stent 200 is located so as to overlap a center position (center) P of the cylindrical portion 130a of the inner balloon 130 in the axial direction. In this manner, when the inner balloon 130 is dilated, it is possible to expand only the central portion of the stent 200 in the axial direction.

As a material for fabricating the stent 200, biocompatible metal is preferably used. For example, the material includes iron base alloy such as stainless steel, tantalum (tantalum alloy), platinum (platinum alloy), gold (gold alloy), cobalt-bases alloy such as cobalt chromium alloy, a titanium alloy, and niobium alloy. In addition, the stent 200 may be a biodegradable stent configured to include polymer as a main material, for example. The material is not particularly limited as long as the material is known as the material of the balloon expandable stent. In addition, a medicine provided with desired medical efficacy may be applied to the stent 200.

The design or configuration of the strut for configuring the stent 200 is not particularly limited. In addition, for example, the stent 200 may be configured to serve as an open cell type, or may be configured to serve as a closed cell type.

Next, a use example of the stent delivery system 10 will be described with reference to FIGS. 4 and 5. Herein, an example will be described in which the stent delivery system 10 is applied to a medical procedure for widening the stenosed site N formed in the blood vessel V. The stent 200 in FIGS. 5(A) to 5(C) is illustrated using an end view.

Figure 4A:
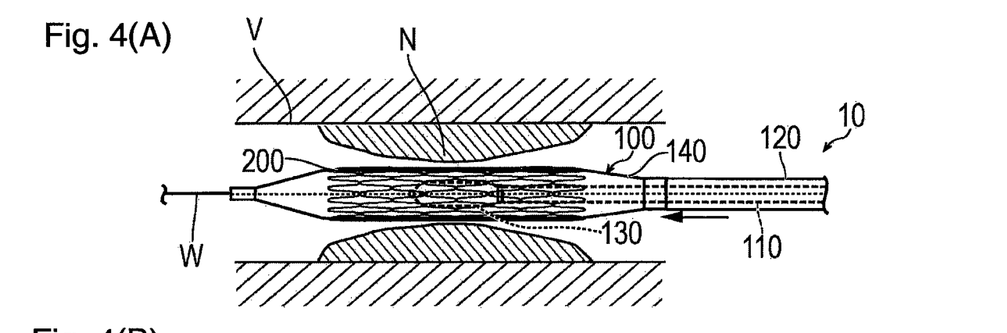
FIG. 4(A) is a view illustrating a state where a distal portion of the stent delivery system is delivered to a stenosed site.
Figure 5A:
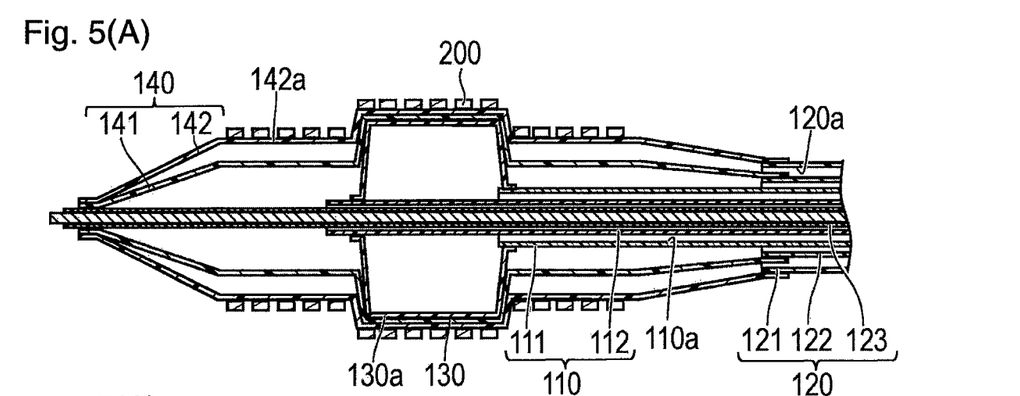
FIG. 5(A) is a view corresponding to FIG. 4(B).

First, as illustrated in FIG. 4(A), the distal portion of the stent delivery system 10 in an initial state is introduced into the blood vessel V along the guide wire W, which was inserted into the stenosed site N beforehand, and the outer balloon 140 having the stent 200 mounted thereon is disposed at the stenosed site N.

Figure 4B:
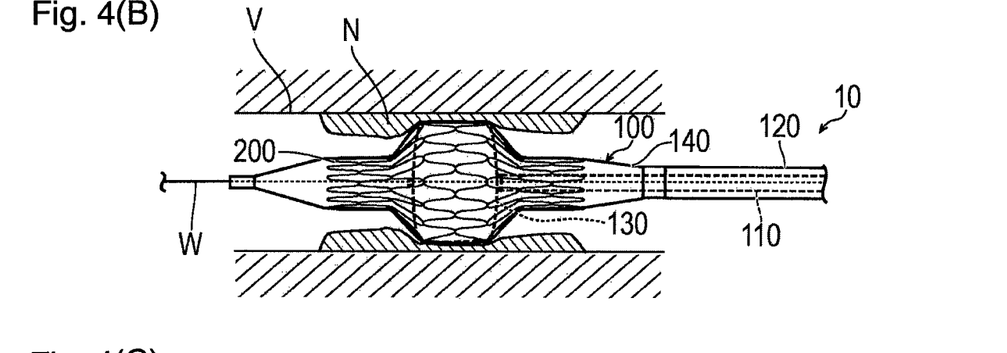
FIG. 4(B) is a view illustrating a state where an inner balloon is dilated.

Subsequently, the pressurizing medium is supplied to the inner balloon dilating lumen 110a via the inner balloon port 150, thereby increasing the internal pressure of the inner balloon 130 up to the nominal pressure and dilating the inner balloon 130 as illustrated in FIG. 4(B). Here, in an initial state, the center position (center) of the stent 200 in the axial direction is located so as to overlap the center position (center) P of the cylindrical portion 130a of the inner balloon 130 (refer to FIG. 2(A)). Therefore, as illustrated in FIG. 5(A), as the inner balloon 130 is dilated, the outer balloon 140 is partially spread outward in the radial direction, thereby expanding only the central portion of the stent 200. In this case, as illustrated in FIG. 4(B), a dilating degree of the inner balloon 130 is adjusted so that the central portion of the stent 200 sufficiently comes into pressing contact with the stenosed site N.

Figure 4C:
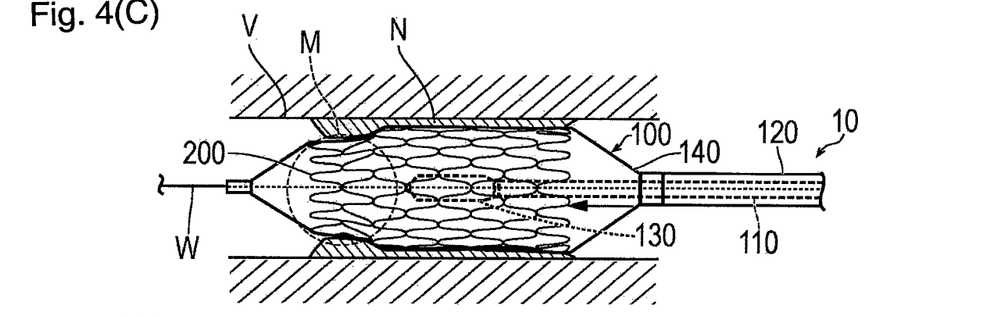
FIG. 4(C) is a view illustrating a state where an outer balloon is dilated.

Subsequently, at least a portion of the pressurizing medium is discharged from the inner balloon 130, thereby deflating the inner balloon 130 once. Thereafter, the pressurizing medium is supplied to the outer balloon dilating lumen 120a via the outer balloon port 160, thereby increasing the internal pressure of the outer balloon 140 up to the nominal pressure and dilating the outer layer 142 of the outer balloon 140 as illustrated in FIGS. 4(C) and 5(B). In this case, as the pressurizing medium moves axially from the central portion toward the end portion, the outer layer 142 of the outer balloon 140 is dilated outward in the radial direction from the central portion toward the axial end portion (distal end portion). As the outer layer 142 of the outer balloon 140 is dilated, the stent 200 gradually expands outward in the radial direction from the central portion toward the axial end portion (distal end portion).

Here, the inner layer 141 of the outer balloon 140 is formed to have the compliance lower than that of the outer layer 142. Accordingly, when the outer layer 142 is deformed in the dilated manner, the inner layer 141 may be inhibited or prevented from being deformed inward in the radial direction. Therefore, the lumen for allowing the inner balloon 130 to move in the axial direction can be maintained inside in the radial direction of the inner layer 141 of the outer balloon 140. Accordingly, in the subsequent medical procedure, the inner balloon 130 can be more smoothly moved in the axial direction.

Although the inner balloon 130 is deflated before the outer balloon 140 is dilated, the configuration or method of use is not limited in this way. The outer balloon 140 may be dilated while the inner balloon 130 is left in a dilated state.

Figure 5B:
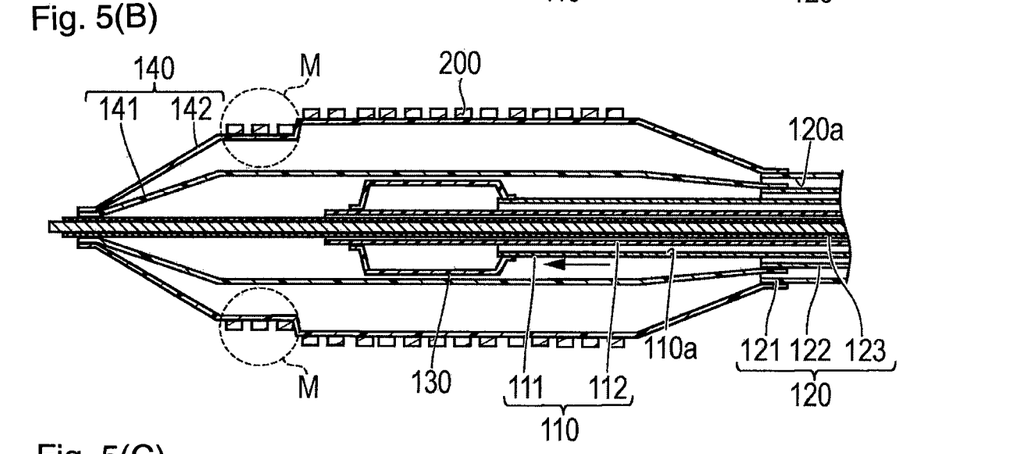
FIG. 5(B) is a view corresponding to FIG. 4(C).
Figure 5C:
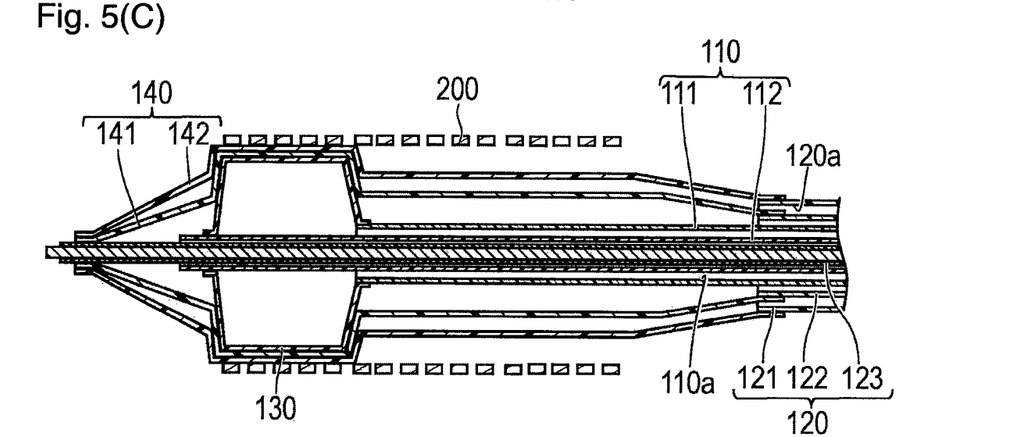
FIG. 5(C) is a view corresponding to FIG. 4(D).

In a case where an insufficiently expanded site (incomplete pressing contact site (Malapposition)) M occurs in the stent 200 as illustrated in a portion surrounded by a broken line in FIGS. 4(C) and 5(B), the insufficiently expanded site M is further expanded, thereby performing supplementary expansion (post expansion) for bringing the stent 200 into pressing contact with the lesion area.

First, at least a portion of the pressurizing medium is discharged from the outer balloon 140, thereby deflating the outer balloon 140. The outer balloon 140 is deflated so as to decrease the dilating force applied to the stent 200 by the outer balloon 140. Accordingly, the stent 200 can be expanded using the dilating force applied by only the inner balloon 130. Therefore, it is possible to inhibit or prevent a force from being inadvertently applied to the stent 200 during the supplementary expansion. Furthermore, the internal pressure of the outer balloon 140 is lowered to a pressure lower than the nominal pressure. In this manner, the dilated diameter of the inner balloon 130 can be deformed to be larger than the dilated diameter of the outer balloon 140. In this manner, the inner balloon 130 can locally expand the insufficiently expanded site M.

Figure 4D:
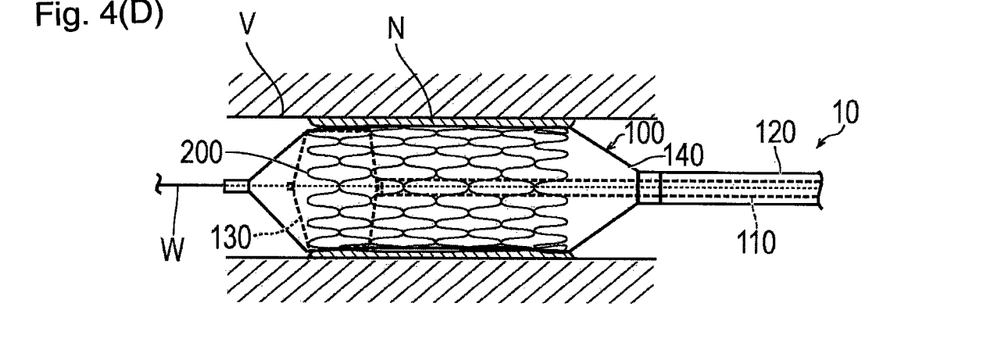
FIG. 4(D) is a view illustrating a state where the inner balloon is moved in an axial direction so as to perform supplementary dilating.

Subsequently, the inner balloon 130 is moved in the axial direction (arrow direction in FIGS. 4(C) and 5(B)) so as to be located in the insufficiently expanded site M of the stent 200. Thereafter, as illustrated in FIGS. 4(D) and 5(C), the pressurizing medium is supplied to the inner balloon dilating lumen 110a so as to dilate the inner balloon 130. As the inner balloon 130 is dilated, the insufficiently expanded site M of the stent 200 is expanded. In this way, the supplementary expansion of the stent 200 can be performed using the stent delivery system 10.

After the medical procedure such as the indwelling and the supplementary expansion of the stent 200 is completed using the stent delivery system 10, the pressurizing medium is discharged so as to deflate the balloons 130 and 140. Then, the balloon catheter 100 is appropriately removed.

In the above-described medical procedure, deflated and dilated states of the balloons 130 and 140 can be appropriately changed. For example, the medical procedure of the above-described supplementary expansion may be carried out without deflating the outer balloon 140 while a dilated state of the outer balloon 140 is maintained. In this manner, while the dilating force applied to the stent 200 by the outer balloon 140 is maintained, the insufficiently expanded site M can be locally expanded by the inner balloon 130. In addition, at least a portion of the outer balloon 140 is in pressing contact with the stenosed site N. Accordingly, the balloon catheter 100 can be positioned and held at a predetermined position. In this manner, it is possible to inhibit or prevent the position deviation from the stenosed site N when the inner balloon 130 is deformed in the dilated manner.

A medical procedure for causing a stent 200 to be indwelled at the stenosed site N by using a stent delivery system 11 according to a comparative example will be described with reference to FIGS. 6(A) to 6(D). The stent delivery system 11 according to the comparative example has a balloon catheter 101 including only one balloon 140a having the stent 200 mounted thereon.

Figure 6A:
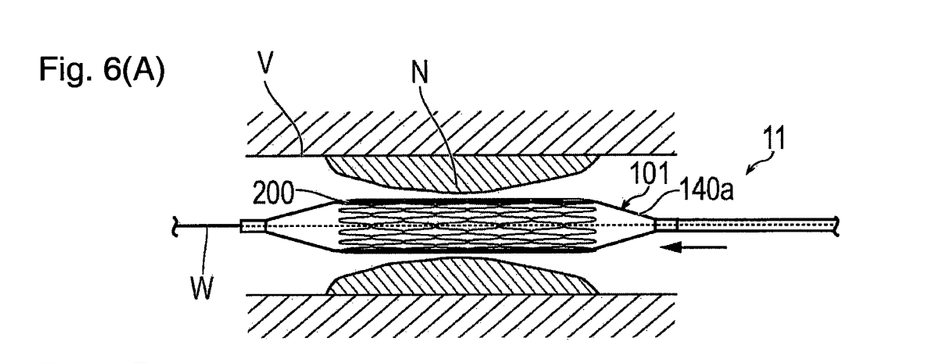
FIG. 6(A) is a view illustrating a state where a distal portion of the stent delivery system is delivered to a stenosed site.

First, as illustrated in FIG. 6(A), the balloon 140a having the stent 200 mounted thereon is disposed in the stenosed site N.

Figure 6B:
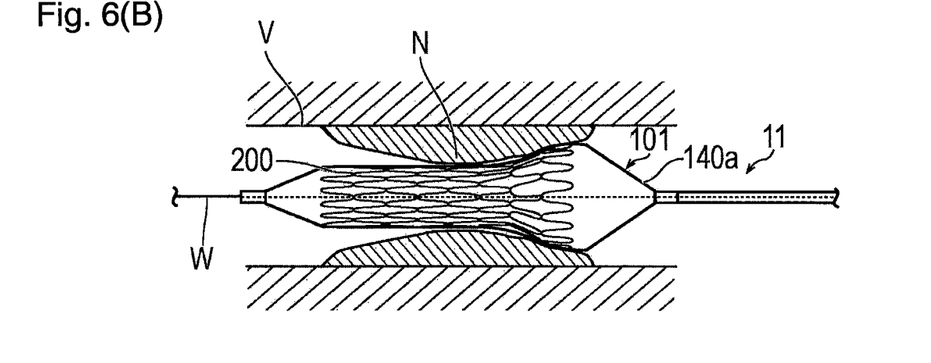
FIGS. 6(B) to 6(D) are views illustrating each state where a balloon is dilated.
Figure 6C:
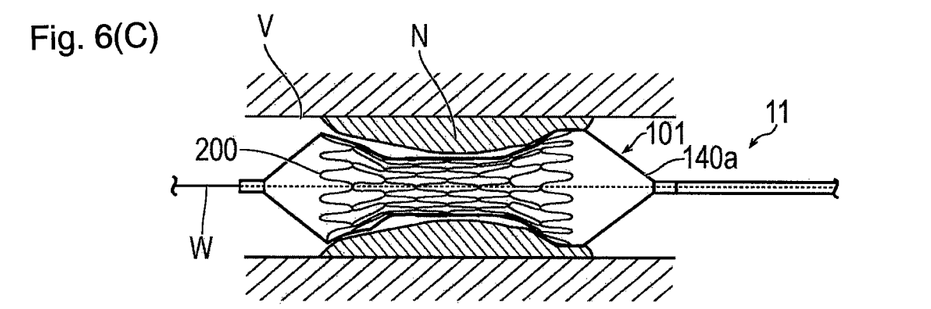
Figure 6D:
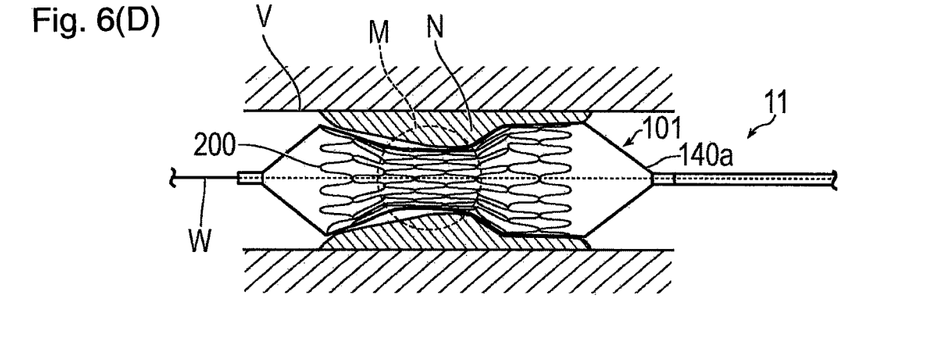

Subsequently, as illustrated in FIGS. 6(B) to 6(D), the pressurizing medium is supplied from the proximal side, thereby dilating the balloon 140a so as to expand the stent 200. Here, generally, the end portion of the stent 200 has few restraint points of the strut, and is more freely movable compared to the central portion. Therefore, in a case where the balloon 140a is dilated and substantially uniform pressure is applied to the stent 200 outward in the radial direction, the end portion of the stent 200 is more likely to be expanded than the central portion. Therefore, the end portion of the stent 200 is expanded earlier than the central portion. In this case, as illustrated in FIG. 6(B), the proximal portion of the stent 200 to which the pressurizing medium is supplied earlier is expanded earlier than the distal portion.

Thereafter, as illustrated in FIG. 6(C), the distal portion of the stent 200 is expanded. Furthermore, if the pressurizing medium is supplied to the balloon 140a, the stent 200 is gradually expanded from the proximal side as illustrated in FIG. 6(D). However, the insufficiently expanded site M of the stent 200 finally appears in the central portion in some cases. This causes insufficient expansion of the stent 200. Therefore, it is necessary to perform the supplementary expansion for expanding the insufficiently expanded site M of the stent 200.

In order to perform the supplementary expansion, another balloon catheter whose dilated diameter is larger than that of the initially expanded balloon catheter 101 is usually used. Therefore, it is necessary to remove the balloon catheter 101 and insert another balloon catheter. A plurality of balloon catheters are prepared and used, thereby increasing the cost and labor which are required for the medical procedure. In addition, the central portion of the stent 200 having the insufficient expansion has a narrow lumen. Accordingly, the balloon catheter for the supplementary expansion cannot be inserted in some cases.

According to the stent delivery system 10 disclosed here by way of the embodiment described above representing one example of the inventive balloon catheter, the central portion of the stent 200 can be expanded earlier than the end portion by the inner balloon 130. Therefore, it is possible to avoid insufficient expansion of the stent 200 by more reliably expanding the central portion of the stent 200 in which the insufficient expansion is likely to appear.

In addition, the medical procedure such as the indwelling of the stent 200 and the supplementary expansion after the indwelling of the stent 200 can be carried out using one balloon catheter 100. Accordingly, it is possible to omit work for inserting another balloon catheter into a living body or work for pulling out another balloon catheter from the living body after the indwelling of the stent 200. Therefore, the treatment can be smoothly, easily, and progressively performed.

An operation according to the present embodiment will be described.

The balloon catheter 100 according to the present embodiment includes the inner balloon shaft (first shaft) 110 that includes the inner balloon dilating lumen (first lumen) 110a enabling the pressurizing medium to circulate therethrough, and that extends in the axial direction, the inner balloon (first balloon) 130 that is disposed on the distal side of the inner balloon shaft 110, and that is capable of being deformed in the dilated manner and being deformed in the deflated manner in the radial direction in response to supply and discharge of the pressurizing medium via the inner balloon dilating lumen 110a, the outer balloon shaft (second shaft) 120 that includes the outer balloon dilating lumen (second lumen) 120a enabling the pressurizing medium to circulate therethrough, and that stretches in the axial direction similarly to the inner balloon shaft 110, and the outer balloon (second balloon) 140 that is disposed on the distal side of the outer balloon shaft 120 so as to cover the outer periphery of the inner balloon 130, and that is capable of being deformed in the dilated manner and being deformed in the deflated manner in the radial direction in response to supply and discharge of the pressurizing medium via the outer balloon dilating lumen 120a. The inner balloon shaft 110 is configured to be movable in the axial direction relative to the outer balloon shaft 120, and the inner balloon 130 is configured to be movable in the axial direction relative to the outer balloon 140 in response to movement of the inner balloon shaft 110.

According to the balloon catheter 100 configured in this way, the inner balloon 130 can be moved in the axial direction relative to the outer balloon 140. Accordingly, the insufficiently expanded site M of the stent 200 can be locally expanded. In this manner, it is possible to inhibit or prevent the insufficient expansion of the stent 200. In addition, one balloon catheter can correspond to treatment performed multiple times, such as indwelling and supplementary expansion of the stent 200. Accordingly, it is possible to reduce the number of balloon catheters to be prepared and used during the medical procedure. In this manner, it is possible to inhibit or prevent poor medical cost performance caused by preparing and using a plurality of balloon catheters.

In addition, the outer balloon 140 has the inner layer 141 which is disposed so as to cover the outer periphery of the inner balloon 130, and the outer layer 142 which is disposed so as to cover the outer periphery of the inner layer 141 and which forms the space communicating with the outer balloon dilating lumen 120a between the inner layer 141 and the outer layer 142. According to this configuration, the pressurizing region of the inner balloon 130 and the pressurizing region of the outer balloon 140 are formed separately from each other. In this manner, the pressurizing medium of the inner balloon 130 and the pressurizing medium of the outer balloon 140 do not mix with each other. Accordingly, for example, it is possible to inhibit or prevent a disadvantage that the pressurizing medium of the outer balloon 140 may flow back to the proximal side through the portion between the inner balloon inner tube 112 and the outer balloon inner tube 123.

In addition, the inner layer 141 of the outer balloon 140 exhibits the compliance lower than that of the outer layer 142. Accordingly, when the outer layer 142 of the outer balloon 140 is deformed in the dilated manner, the inner layer 141 of the outer balloon 140 can be inhibited or prevented from being pressed by the pressurizing medium and deformed inward in the radial direction. In this manner, the lumen for allowing the inner balloon 130 to move in the axial direction can be maintained inside in the radial direction of the inner layer 141 of the outer balloon 140. Accordingly, the inner balloon 130 can be more smoothly moved in the axial direction.

In addition, the dilated diameter of the inner balloon 130 when the internal pressure is the nominal pressure is larger than the dilated diameter of the outer balloon 140 when the internal pressure of the outer balloon 140 reaches the nominal pressure. Accordingly, an insufficiently widened or enlarged site of the stent 200 can be locally expanded by the inner balloon 130.

In addition, the inner balloon 130 exhibits the compliance lower than that of the outer balloon 140. In this manner, the inner balloon 130 has the pressure resistance higher than that of the outer balloon 140. Accordingly, compared to the outer balloon 140, the stronger dilating force can be locally applied to the stent 200.

In addition, the balloon catheter 100 is a stent delivery balloon catheter in which the stent 200 is mounted on the outer balloon 140 in a deflated state. In a state where the stent 200 is mounted on the outer balloon 140, the center position (center portion) of the stent 200 overlaps the center position (center) P of the inner balloon 130 in the axial direction of the inner balloon shaft 110. The inner balloon 130 is dilated earlier than the outer balloon 140. In this manner, the central portion of the stent 200 which is relatively less likely to be expanded can be expanded earlier than the end portion. In addition, after the outer balloon 140 is dilated, the insufficiently expanded site of the stent 200 can be supplementarily expanded by the inner balloon 130.

In this case, the inner balloon 130 can be moved in the axial direction. Accordingly, only the insufficiently expanded site M can be locally expanded. In this manner, it is possible to prevent the insufficient expansion of the stent 200.

Modification Example

Next, a balloon catheter 300 according to a modification example will be described. In describing the modification example, features in the modification example that are the same or similar to those in the embodiment described above are identified by the same reference numerals, and a detailed description of such features is not be repeated. In addition, configurations which are not particularly described herein can be adopted, similarly to the configurations of the above-described embodiment.

The balloon catheter 100 according to the above-described embodiment is configured to serve as the stent indwelling balloon catheter in which the stent 200 is mounted on the outer balloon 140. In contrast, the balloon catheter 300 according to the modification example is configured to serve as a balloon catheter for treating a stenosed site which is used in order to widen the stenosed site N inside the body lumen such as the blood vessel V. That is, the stent 200 is not mounted on the balloon catheter 300.

Figure 7:
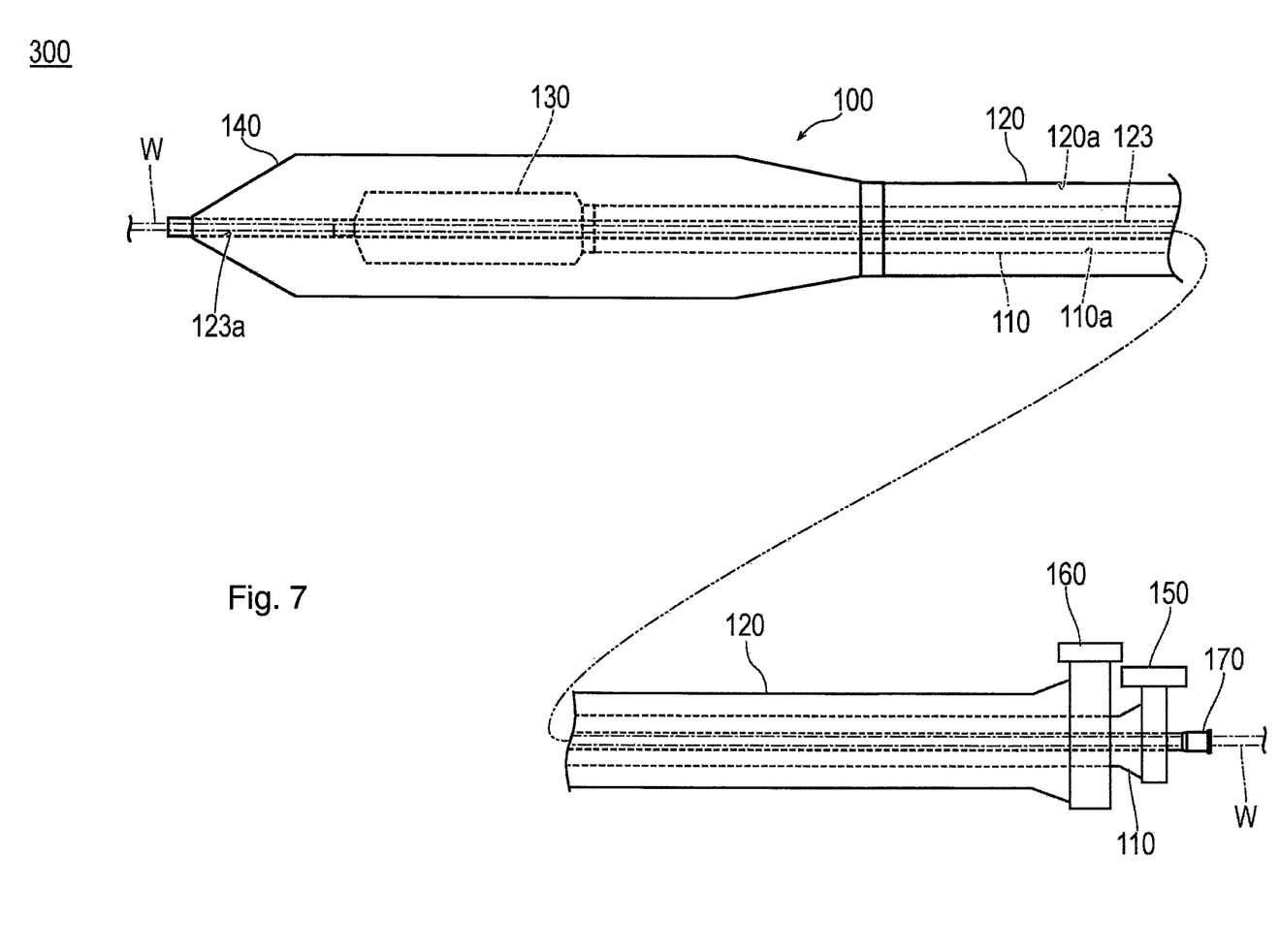
FIG. 7 is a view illustrating an overall configuration of a balloon catheter according to a modification example.

As illustrated in FIG. 7, the balloon catheter 300 according to the modification example has substantially the same configuration as that of the balloon catheter 100 according to the above-described embodiment. Therefore, a detailed description of the balloon catheter 300 will not be repeated.

A use example of the balloon catheter 300 will be described with reference to FIG. 8.

Figure 8A:
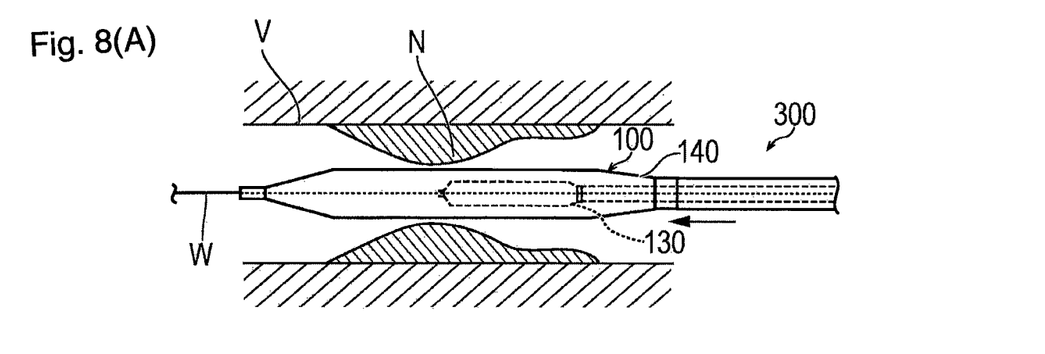
FIG. 8(A) is a view illustrating a state where a distal portion of the balloon catheter is delivered to a stenosed site.

First, as illustrated in FIG. 8(A), the distal portion of the balloon catheter 300 is introduced into the blood vessel V along the guide wire W inserted into the stenosed site N in advance, and the outer balloon 140 is disposed in the stenosed site N.

Figure 8B:
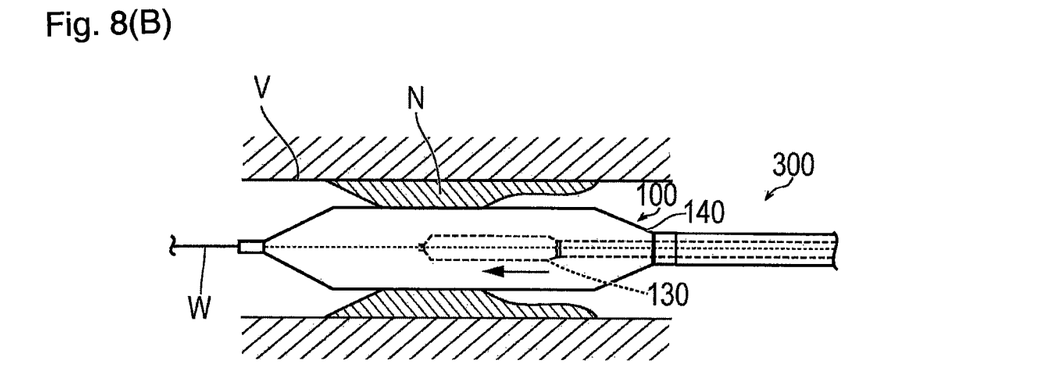
FIG. 8(B) is a view illustrating a state where an outer balloon is dilated.

Subsequently, as illustrated in FIG. 8(B), the pressurizing medium is supplied to the outer balloon dilating lumen 120a via the outer balloon port 160 so as to dilate the outer balloon 140. The outer surface of the outer balloon 140 is dilated and pressed against the stenosed site N formed in the blood vessel V, and the stenosed site N is spread Or widened. Thereafter, the inner balloon 130 is moved in the axial direction (arrow direction in FIG. 8(B)), and is disposed again in an insufficiently widened site of the stenosed site N.

Figure 8C:
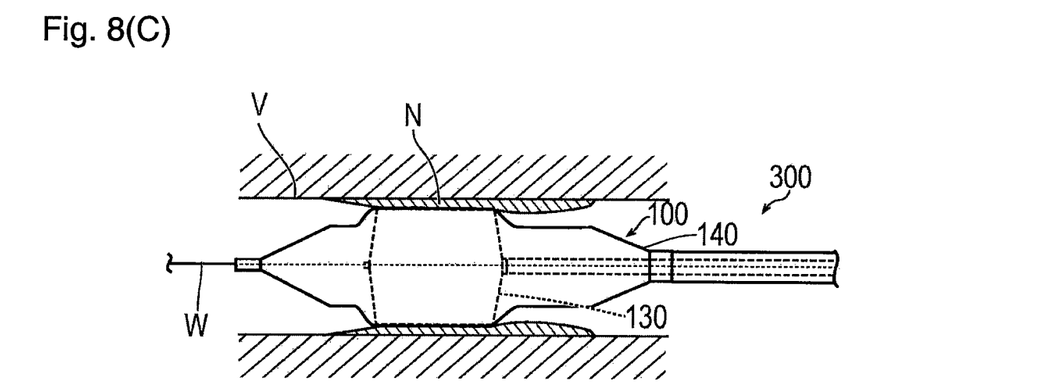
FIG. 8(C) is a view illustrating a state where an inner balloon is dilated.

Subsequently, as illustrated in FIG. 8(C), the pressurizing medium is supplied to the inner balloon dilating lumen 110a via the inner balloon port 150, and the inner balloon 130 is dilated. In this case, the inner balloon 130 is dilated so that the dilated diameter becomes larger than that of the outer balloon 140. In this manner, dilating the inner balloon 130 further dilates the outer balloon 140, thereby spreading or expanding the stenosed site N. The outer balloon 140 may be deflated before the inner balloon 130 is dilated.

The inner balloon 130 is formed to have the compliance lower than that of the outer balloon 140. Accordingly, the inner balloon 130 has high pressure resistance. Therefore, even in a case where the calcification of the stenosed site N has progressed, the outer balloon 140 can be reliably dilated by the dilation of the inner balloon 130. In this way, the inner balloon 130 can be dilated using so-called low-compliant characteristics.

After widening by the balloon catheter 300 is completed, the pressurizing medium is discharged, and the balloons 130 and 140 are deflated. Then, the balloon catheter 300 is appropriately removed.

The medical procedure to which the balloon catheter 300 according to the modification example is applicable is not limited to the above-described use example. For example, it is also possible to use the balloon catheter 300 in treatment for widening or expanding the stenosed site N before the stent indwells the stenosed site N (pre-widening).

As described above, the balloon catheter 300 according to the modification example is the balloon catheter for treating the stenosed site which is used in widening the stenosed site N inside the body lumen. For example, the balloon catheter 300 is used in carrying out the medical procedure for dilating the inner balloon 130 after the outer balloon 140 is dilated. In this case, at least a portion of the outer balloon 140 is in pressing contact with the stenosed site N. Accordingly, the balloon catheter 300 can be positioned and held at a predetermined position. In this manner, it is possible to prevent the position deviation from the stenosed site N when the inner balloon 130 deformed in the dilated manner. In this way, the stenosed site N can be more reliably widened or expanded by appropriately adjusting the timing for dilating the balloons 130 and 140. One balloon catheter 300 enables work for widening or expanding the stenosed site N to be carried out multiple times. Accordingly, it is possible to omit work for inserting the balloon catheter 300 into the living body or work for pulling out the balloon catheter 300 from the living body. Therefore, the treatment can be smoothly, easily, and progressively performed. In addition, the inner balloon 130 is moved in the axial direction. In this manner, the stenosed site N to be widened can be locally widened. In addition, the number (type) of balloon catheters used in carrying out the medical procedure once can be reduced. In this manner, it is possible to improve medical cost performance in carrying out the medical procedure using the balloon catheter 300.

Hitherto, the balloon catheter disclosed here has been described with reference to the embodiment and the modification example. However, the present invention is not limited only to the configurations described in the embodiment and the modification example. Based on the description in claims, the present invention can be appropriately changed.

For example, the outer balloon is not limited to a double layer structure including the inner layer and the outer layer, and may be formed to have only one layer. In this case, it is preferable to dispose a seal member between the inner tube of the outer balloon and the inner tube of the inner balloon so as to prevent the pressurizing medium from flowing back to the proximal side inside the outer balloon.

In addition, the inner layer of the outer balloon is formed to have the compliance lower than that of the outer layer of the outer balloon. However, the configuration is not particularly limited as long as the inner layer can be inhibited or prevented from being deformed inward in the radial direction, when the outer layer of the outer balloon is deformed in the dilated manner. For example, a member for preventing the inner layer of the outer balloon from being deformed inward in the radial direction may be separately provided.

In addition, a structure of each portion or an arrangement of members of the stent delivery system or the balloon catheter described in the above-described embodiment and modification example can be appropriately changed. It is possible to omit the use of the additional members described with reference to the drawings, or it is possible to appropriately use other additional members.

In addition, the shape and the configuration of the stent in the stent delivery system are not limited to the configurations described in the above-described embodiment and the accompanying drawings. A known stent can be used as the balloon expandable stent.

The detailed description above describes embodiments of a balloon catheter and method representing examples of the inventive catheter and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
    a first shaft that includes a first lumen enabling a pressurizing medium to circulate therethrough, and that extends in an axial direction;
    a first balloon disposed on a distal side of the first shaft, the first balloon being deformable in a radially expandable manner in response to supply of the pressurizing medium to the first balloon via the first lumen and being deformable in a radially contractible manner in response to discharge of the pressurizing medium from the first balloon via the first lumen;
    a second shaft that includes a second lumen enabling the pressurizing medium to circulate therethrough, and that extends in the axial direction;
    a second balloon disposed on a distal side of the second shaft and covering an outer periphery of the first balloon, the second balloon being deformable in a radially expandable manner in response to supply of the pressurizing medium to the second balloon via the second lumen and being deformable in a radially contractible manner in response to discharge of the pressurizing medium via the second lumen;
    the first shaft being movable in the axial direction relative to the second shaft;
    the first balloon being movable in the axial direction relative to the second balloon in response to movement of the first shaft, and
    the second balloon comprises an inner layer and an outer layer, the inner layer possessing an outer periphery and covering the outer periphery of the first balloon, the outer layer covering the outer periphery of the inner layer, and a space between the inner layer and the outer layer that communicates with the second lumen.

2. The balloon catheter according to claim 1, wherein the inner layer of the second balloon has a compliance lower than that of the outer layer.

3. The balloon catheter according to claim 1, wherein a dilated diameter of the first balloon when an internal pressure of the first balloon reaches nominal pressure is larger than a dilated diameter of the second balloon when an internal pressure of the second balloon reaches nominal pressure.

4. The balloon catheter according to claim 1, wherein the first balloon is less compliant than the second balloon.

5. The balloon catheter according to claim 1,
    the balloon catheter being used for stent delivery by mounting a stent on the second balloon while the second balloon is in a deflated state, and
    in a state in which the stent is mounted on the second balloon, a center position of the stent overlaps a center position of the first balloon in the axial direction of the first shaft.

6. The balloon catheter according to claim 1, wherein the balloon catheter is used to expand a stenosed site inside a body lumen in order to treat the stenosed site.

7. The balloon catheter according to claim 1, wherein the first balloon possesses opposite axial ends fixed to respective shafts and the second balloon possesses opposite axial ends fixed to respective shafts, the first balloon possessing an axial length between the opposite axial ends of the first balloon in the axial direction, the second balloon possessing an axial length between the opposite axial ends of the second balloon in the axial direction, the axial length of the first balloon being shorter than the axial length of the second balloon.

8. A balloon catheter positionable in a blood vessel, the balloon catheter comprising:
    a first balloon possessing an interior and being radially expandable in response to supply of a pressurizing medium to the interior of the first balloon, the first balloon being radially contractible in response to discharge of the pressurizing medium from the interior of the first balloon;
    a second balloon positioned in covering relation to the first balloon so that the first balloon is positioned inside the second balloon, the second balloon possessing an interior and being radially expandable in response to supply of the pressurizing medium to the interior of the second balloon, the second balloon being radially contractible in response to discharge of the pressurizing medium from the interior of the second balloon;
    a first lumen in communication with the interior of the first balloon to supply the pressurizing medium to the interior of the first balloon and to discharge the pressurizing medium from the interior of the first balloon;
    a second lumen in communication with the interior of the second balloon to supply the pressurizing medium to the interior of the second balloon and to discharge the pressurizing medium from the interior of the second balloon, the second lumen being separate from the first lumen;

the first balloon being axially movable relative to the second balloon to position the first balloon at different positions relative to the second balloon;

the first balloon being less compliant than the second balloon; and the second balloon comprises an inner layer and an outer layer, the inner layer being positioned radially between the outer layer and the first balloon, and further comprising a space between the inner layer and the outer layer that communicates with the second lumen.

9. The balloon catheter according to claim 8, wherein the first balloon is mounted on a first shaft, the first lumen passing through the first shaft.

10. The balloon catheter according to claim 9, wherein the second balloon is mounted on a second shaft, the second lumen passing through the second shaft.

11. The balloon catheter according to claim 8, wherein the inner layer and the outer layer each possess a respective compliance, the compliance of the inner layer being different from the compliance of the outer layer.

12. The balloon catheter according to claim 8, wherein the inner layer, the outer layer and the first balloon each possess a respective compliance, the compliance of the inner layer being different from the compliance of the outer layer and being different from the compliance of the first balloon.

13. The balloon catheter according to claim 8, wherein the inner layer possesses a lesser compliance than the outer layer and a greater compliance than the first balloon.

14. The balloon catheter according to claim 8, wherein the first balloon is axially movable relative to the second balloon.

15. A balloon catheter comprising:

a first shaft that includes a first lumen enabling a pressurizing medium to circulate therethrough, and that extends in an axial direction;

a first balloon disposed on a distal side of the first shaft, the first balloon being deformable in a radially expandable manner in response to supply of the pressurizing medium to the first balloon via the first lumen and being deformable in a radially contractible manner in response to discharge of the pressurizing medium from the first balloon via the first lumen;

a second shaft that includes a second lumen enabling the pressurizing medium to circulate therethrough, and that extends in the axial direction;

a second balloon disposed on a distal side of the second shaft and covering an outer periphery of the first balloon, the second balloon being deformable in a radially expandable manner in response to supply of the pressurizing medium to the second balloon via the second lumen and being deformable in a radially contractible manner in response to discharge of the pressurizing medium via the second lumen;

the first shaft being movable in the axial direction relative to the second shaft;

the first balloon being movable in the axial direction relative to the second balloon in response to movement of the first shaft; and the first balloon possessing opposite axial ends fixed to respective shafts and the second balloon possessing opposite axial ends fixed to respective shafts, the first balloon possessing an axial length between the opposite axial ends of the first balloon in the axial direction, the second balloon possessing an axial length between the opposite axial ends of the second balloon in the axial direction, the axial length of the first balloon being shorter than the axial length of the second balloon.

16. The balloon catheter according to claim 15, wherein the second balloon comprises an inner layer and an outer layer, the inner layer of the second balloon having a compliance lower than that of the outer layer of the second balloon.

17. The balloon catheter according to claim 15, wherein a dilated diameter of the first balloon when an internal pressure of the first balloon reaches nominal pressure is larger than a dilated diameter of the second balloon when an internal pressure of the second balloon reaches nominal pressure.

18. The balloon catheter according to claim 15, wherein the first balloon is less compliant than the second balloon.

19. The balloon catheter according to claim 15, wherein the second balloon comprises an inner layer, an outer layer, and a space between the inner layer and the outer layer.

* * * * *